United States Patent [19]

Bailitis

[11] 4,170,892

[45] Oct. 16, 1979

[54] METHOD OF AND APPARATUS FOR THE ANALYSIS OF GASES

[75] Inventor: Eduard Bailitis, Aachen, Fed. Rep. of Germany

[73] Assignee: Kernforschungsanlage Jülich GmbH, Jülich, Fed. Rep. of Germany

[21] Appl. No.: 903,066

[22] Filed: May 5, 1978

[30] Foreign Application Priority Data

May 6, 1977 [DE] Fed. Rep. of Germany ....... 2720300

[51] Int. Cl.² ............................................ G01N 31/00
[52] U.S. Cl. .......................................... 73/23; 73/30; 250/289
[58] Field of Search ...................... 73/23, 30; 250/281, 250/288, 289, 457; 23/232 R, 254 R

[56] References Cited

U.S. PATENT DOCUMENTS 3,355,587  11/1967  Jenckel ................................... 73/23

OTHER PUBLICATIONS

Pratt et al., "Torsion-Effusion Apparatus for Study of Vapour Pressures of Alloys", *Journal of Scientific Instr.*, vol. 36, p. 465, Nov. 1959.

McKnobbs; "Mass Spectrometric Determination of Oxygen at Partial Pressures of Less Than 1.5 μPa(10⁻⁸Torr)"; General Electric Vacuum Products vol. 23, No. 11, Nov. 1973, pp. 391-394.

*Primary Examiner*—Stephen A. Kreitman
*Attorney, Agent, or Firm*—Karl F. Ross

[57] ABSTRACT

The mean molecular velocity or molecular weight of an unknown gas is determined by admitting the gas at a constant flow rate into an evacuated chamber of known volume, the gas being permitted to escape through a first flow cross section in a Knudsen flow. After a first steady state is reached, the gas density is measured and then a second flow cross section is opened between the evacuated chamber and a low-pressure zone. The measurement is repeated and the difference between the two values obtained and the gradient of the measurement is used to calculate the mean molecular velocity and the molecular weight.

23 Claims, 4 Drawing Figures

METHOD OF AND APPARATUS FOR THE ANALYSIS OF GASES

FIELD OF THE INVENTION

The present invention relates to a method of and an apparatus for the analysis of gases by their mean molecular velocity.

BACKGROUND OF THE INVENTION

It is known that one can determine the density of a gas from the velocity at which it flows through an opening, provided that the opening has a diameter which is relatively small by comparison to the mean free path of the gas molecules. In these systems, the effusion of a reference gas is compared with that of the gas to be analyzed. In accordance with Graham's Law, the square of the effusion velocity is inversely proportional to the gas density.

Using an effusometer of the Bunsen-Schilling type, reference gas and the gas to be analyzed are successively introduced or simultaneously introduced into one or two vessels which are pressurized. The duration over which the gas flows out of the vessel or vessels through the fine openings is determined.

From the results thus obtained, based upon thermodynamic and gas-kinetic considerations, the atomic or molecular weight and other parameters can be readily calculated.

The precision of the conventional effusion method is, however, unsatisfactory and the amount of material of the samples which must be handled is excessive for use of the technique and measurements in atomic physics.

OBJECT OF THE INVENTION

It is, therefore, the principal object of the present invention to provide a method of and a device for analyzing gases which are capable of high precision, which are relatively simple and which make use of small samples suitable for exploitation of the technique in the realm of atomic physics.

SPECIFIC DESCRIPTION

According to the present invention, a reference gas and a gas to be analyzed are mixed in definite proportions per unit time in a first zone of predetermined volume and the mixture is forced from the first zone in a Knudsen flow with variable effective cross section into a second zone at predetermined pressure, the gas quantities or a parameter proportional thereto in the first zone upon attainment of a first steady state being measured. The effective cross section of the Knudsen flow is spontaneously altered and a corresponding measurement for the secondary state thereafter attained is made, and the difference between values measured at the two stationary states as well as the gradient of the measured values as a function of the change in cross section are determined.

Preferably, the change in the effective cross section is a change in the direction of cross-sectional enlargement, i.e. the cross section is increased from the first steady state to the second steady state at which the two successive measurements are taken. The detected data or measurements can be evaluated simply when the volume in the first zone, the pressure in the second zone and the gas flow rate in the first zone are all maintained constant.

It is also preferred to obtain a series of measurements with the cross-sectional change being effected between them and the gradient and difference between the new and the previous stationary state obtained for each pair of stationary states and for each set of measurements.

The changing, especially increase, in the effective cross section of the Knudsen flow preferably is effected by the same amount or factor from one set of measurements to the next. This enables a calculator or computer to evaluate the results readily, even when a variable adjustment of the effective Knudsen flow cross section is provided.

The aforementioned measured values, especially their differences, and the gradients of the changes in values, will generally be parameters of the gas density obtained directly. However, it is possible to obtain values which are proportional thereto, especially when the gas consists of or contains charged particles. In this case, the number of charges may be detected. With radioactive gases, the radiation intensity may be detected. In the first case, using an appropriate transducer, an electrical signal can be provided which represents the desired measured value.

Whether it is the directly measured gas parameter itself or an electrical signal representing the gas parameter, the value may be applied as a signal to the computer or calculator which can be designed to evaluate the measurements in accordance with the requisite equations.

Naturally, in gas analysis, the determination of the molecular weight or the relative mole mass are of principal importance.

In accordance with the Maxwell distribution law, the square of the mean molecular velocity is dependent upon the molecular weight in accordance with the following equation:

$$\bar{w}^2 = (8RT/\pi M) \tag{1}$$

In this equation:
$\bar{w}$ = mean molecular velocity
$R$ = universal gas constant
$T$ = absolute temperature (Kelvin)
$M$ = molecular weight As a consequence, the molecular weight of two different gases is inversely proportional to the square of their mean molecular velocities.

Until the pressure is reduced to several Torr the quantity of gas flowing through an orifice or obstruction is proportional to the mean gas pressure in accordance with the Hagen-Parseuillet law. At lower pressures, however, the throughflow reaches a mean and the pressures of about 0.001 Torr become constant and practically independent of further reduction in pressure. In regions of this "Knudsen flow" regime (high values of Knudsen number) free molecular or slip flow exists so that the mean free path of the gas molecules is at least several centimeters and there is practically no internal friction of the gas.

It is this phenomenon which is exploited by the present invention.

Preferably, the pressure at which the analysis is carried out according to the invention is a vacuum of about $10^{-5}$ to $10^{-9}$, preferably about $10^{-7}$, Torr. In this region, the mean free path of the gas molecules is greater than the apparatus (chamber) dimensions. Nevertheless, such pressures are economically attainable and can be generated or maintained without particular technical difficulties.

Usually the gas is permitted to flow without any externally applied influence through the vacuum zone so that in the effective cross section, apart from the area, there are no other parameters of significance. However, according to a feature of the invention, it is possible to distinguish different types of gas particles during their passage through vacuum zone by subjecting them to the influence of electrical or magnetic fields, passibly after prior excitation by ionization or irradiation with infrared or ultraviolet light etc.

The quotient A of the effective cross section (i.e. the area of a single flow cross section or the sum of the areas of a plurality of flow cross section) and the volume of the first zone $$A = (\sigma + \sigma_1 + \sigma_2)/v$$

A = the constant
$\sigma$ = first cross section
$\sigma_1, \sigma_2 ...$ = further cross sections
v = volume of first zone is always constant. This constant will be referred to subsequently.

The effective cross section affects directly the throughput of the gas, i.e. the volume rate of flow, and hence the time required to reach the desired analysis. Thus, the smaller the effective cross section, the greater is the resolution although the measurable density difference is also smaller. Thus a compromise must be found between the effective cross section and the desire to have a marked intensity difference between the measurements.

For the evaluation of the measurement curves in which, as will be described in greater detail below, one generally must make use of an exponential relationship (i.e. an e-function or a tangential function), it is advantageous to make use of a modern electronic calculator when a graphical rendition using semilogarithmic scales giving straight line results is not suitable or sufficient.

A device for carrying out the process of the present invention will comprise a vacuum chamber of a predetermined (defined) volume V which can be supplied with gas from a source connected therewith. The vacuum chamber is connectible by at least two selectively openable and closable, but independent, valves to a suction pump. A sensor is provided in this chamber to determine the gas density prevalent therein.

Advantageouly, the auxiliary valves have the same effective (flow) cross sections.

Since the invention makes use of the mean molecular velocity of a gas, it can have applications wherever this gas kinetic parameter is of significance. The gas flow involved is small, i.e. of the order of about $10^{13}$ molecules per second.

A preferred use of the system of the invention is in combination with a mass spectrometer which thus can be complemented by the device of the invention. The measured values permit a clear correlation of the spectral lines. The method can thus readily distinguish which molecules are associated with which lines in the mass spectrum.

An important field of use of the present invention is in the mass-spectrometry analysis of organic substances. In the ion source an organic molecule can be broken down into many radicals or fractions, thereby producing a line-rich spectrum. The lines of the parent molecules are frequently not as intense as the secondary lines. With the aid of the invention, one can readily determine which molecules the secondary lines are associated with and thereby obtain further information for structural analysis.

In inorganic fields, the methods can be used for the analysis of clusters. Furthermore it is possible to determine molecular weight or mole mass rapidly and precisely, i.e. in the study of coal gasification. With known molecular velocities or mole mass one can conversely make deductions as to the nature of the gas so that the system can be used in reaction-kinetic and petrochemical fields as well. Because the device according to the invention can be made relatively strong and capable of withstanding mechanical and like stresses, it can be provided directly in a nuclear reactor for gas analysis.

According to yet another feature of the invention, the chamber is pumped out through a valve of larger cross section than the two auxiliary valves having the same flow cross section. The apparatus may be constructed as an ultrahigh vacuum apparatus and the sensor of the system may be constituted by the ion source of an associated mass spectrometer. The mass spectrometer can be traversed by the stream of molecules generally in an axial direction, although it is also possible to direct the molecule stream so that the mass spectrometer lies normal thereto. It has also been found to be advantageous to reduce the pressure in the measuring chamber by 10% to 20% lower than that in the low chamber.

BRIEF DESCRIPTION OF THE DRAWING

The above and other objects, features and advantages of the present invention will become more readily apparent from the following description, reference being made to the accompanying drawing in which.

SPECIFIC DESCRIPTION AND EXAMPLES

Figure 1:
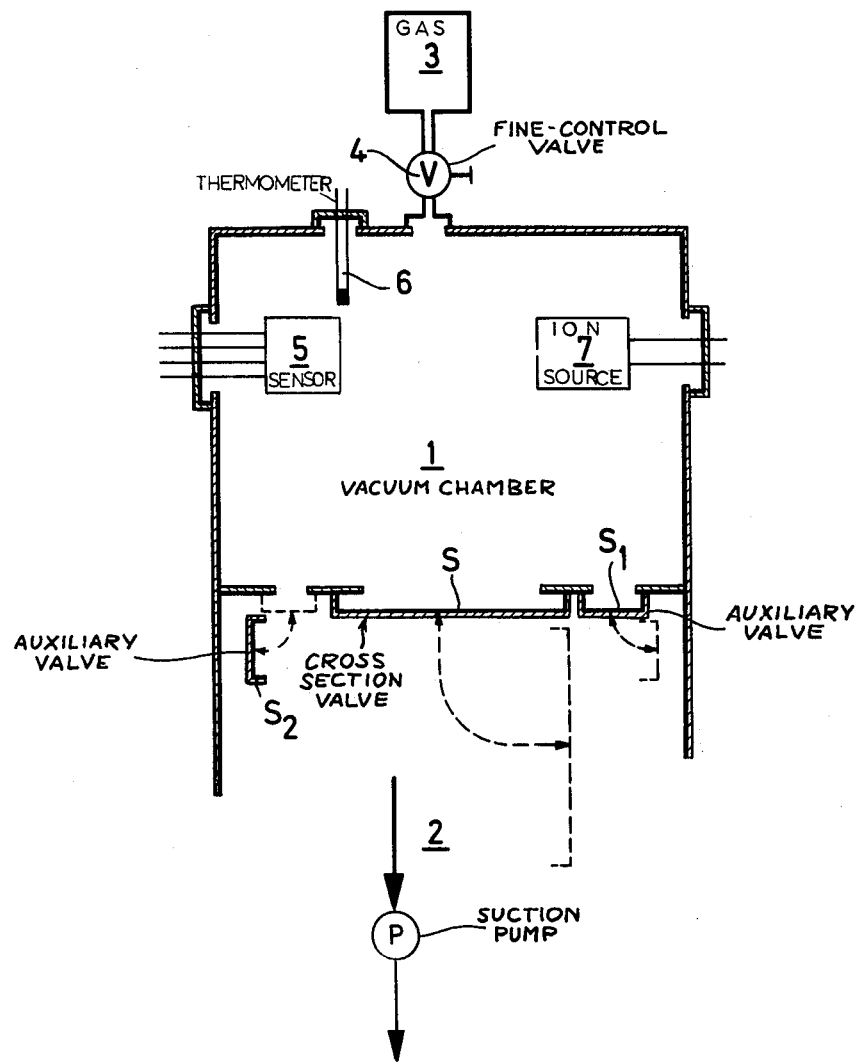
FIGS. 1 to 4 are diagrammatic illustrations of apparatus for carrying out the method of the present invention according to several embodiments thereof.

FIG. 1 shows a vacuum chamber 1 with a defined volume V which is connected as represented by the arrow 2 to a high-power vacuum pump via a large-cross section opening (valve S).

Apart from this main valve S, there are interposed between the vacuum chamber 1 and the pump 2, a pair of auxiliary valves $S_1$ and $S_2$ which can be opened and closed independently of one another, but which can have in their open positions, the same effective cross sections $\sigma_1$ and $\sigma_2$.

A gas-supply source 3 is connected with the inlet of chamber 1 through a fine-control valve 4. Preferably the entire device is constituted as an ultrahigh-vacuum apparatus.

The inflow rate of the gas at N molecules per second is so measured and the pressure in the chamber established that, when the main valve S is closed and one auxiliary valve is open, a pure Knudsen flow results. Advantageously the pressure is held at $10^{-5}$ to $10^{-9}$ Torr.

The inflow rate N is held constant by the control valve 4. After a given time, a stationary (steady) state develops wherein the number of molecules entering the chamber 1 equals the number withdrawn by pump 2. The power of pump 2 must be such that a backflow from the pump to the chamber 1 is excluded.

At a location in the chamber 1 or in an antechamber or fitting connected thereto, there is provided a sensor 5 which generates an electric signal J(e.g. a current amplitude) which is proportional to gas density and wherein:

$$J = k\,c \quad (2)$$

This signal is applied to a measuring or monitoring instrument or to a graphic display (e.g. a pen recorder). In equation (2):

J = electric signal amplitude
k = proportionality or calibration constant
c = gas density.

The sensor 5 can be a conventional device which measures an electric, magnetic, optical or radioactive parameter or characteristic of the gas proportional to gas density. For example, the gas can be ionized and the ion current, which is a function of gas density, can be measured. The measuring instruments are selected such that their time constants are smaller, preferably by several orders of magnitude, than the resultant time constant $4V/\sigma \cdot \overline{w}$ determined by the effective opening $\sigma$ and the volume V in the analysis temperature T. Naturally, the apparatus must be dimensioned accurately.

A constant signal $J_a$ at the output of sensor 5 indicates the establishment of the steady or stationary state. After this steady state value $J_a$ is obtained, the second auxiliary valve is spontaneously opened and the time measured. The gas density in the chamber 1 falls until a new steady state is reached with a sensor output $J_e$. The progress of this can be monitored with the graphic (pen) recorder. The difference $\Delta J$:

$$\Delta J = J_a - J_e \quad (3)$$

can be determined directly experimentally. The change in the measured value upon spontaneous opening following an exponential function.

The change in the measured value from t=0 (inception of the time count at opening of the second auxiliary valve) is:

$$(dJ/dt)_{t=0} \quad (4)$$

This parameter is graphically indicated by the recorder curve or can be determined by a calculator or computer supplied with the measured values or signals representing same directly.

From the two parameters $\Delta J$ and $(dJ/dt)_{t=0}$ and the apparats constant A (which is independent of the nature of the gas), $\overline{w}$, the mean molecular velocity at a constant absolute temperature T can be determined:

$$\frac{4(dJ/dt)_{t=0}}{\Delta J \cdot \overline{w}} \quad (5)$$

In FIG. 1 a thermometer is shown at 6 to extend into the chamber 1 and the ion source is represented at 7 and can be, for example, a tritium ionizing-radiation generator or electric arc.

The mean molecular velocity $\overline{w}$ can be calculated from equation (1) supra when the molecular weight of the gas is known. Thus, to determine the apparatus constant A it is merely necessary to measure the parameters $\Delta J$ and $(dJ/dt)_{t=0}$ according to equations (3) and (4) for a known gas, for example.

Thereafter, the unknown gas is passed through the device at the same absolute temperature T and the parameters $\Delta J$ and $(dJ/dt)_{t=0}$ are determined in accordance with equations (3) and (4). The molecular velocity is then determined by equation (5) and the molecular weight by equation (1).

The invention is of special advantage in a mass spectrometer. The ion source of apparatus mass spectrometer is so adjusted that the electric output signal is proportional to the partial gas density in a given pressure range. The mass spectrometer can thus serve as the sensor. For each ion type generated by the ion source, a line is produced in the mass spectrometer and the mole mass can be calculated for each line. Gas molecules which are transformed into ions in the mass spectrometer can undergo significant physical and chemical changes. The spectrometer is thus usually richer in lines than the gas composition is in molecules of different type.

To determine the apparatus constant, one first uses the oxygen line, carrying out the measurements above described. Then one obtains the measurements for the other line, using the respective $\overline{w}$ values given by the respective mole mass obtained from the mass spectrometer. For all regular gases flowing through the vacuum chamber, one and the same apparatus constant A will be obtained. When a line is evaluated which corresponds to a fragmentary ion generated in the ion source, having a short life, and not participating in the gas flow, the apparatus constant will not be the value A but will be a smaller value B. These values determine the relationship $A/B = \sqrt{yl}$ where yl is the separation factor of the parent molecule. This gives additional information as to the lines of the mass spectrum.

The invention can also be used for the detection of clusters. Clusters are large molecules composed of associations of smaller molecules. If CD is a diagrammatic gas molecule, it may form gas-cluster molecules $(CD)_x$ where x is the number of individual molecules in a cluster. The cluster is held together by the relatively small binding energy of van der Wall's forces. In the ion source a cluster breaks up completely or partially into its components and scarcely has an independent line in the spectrum.

Figure 2:
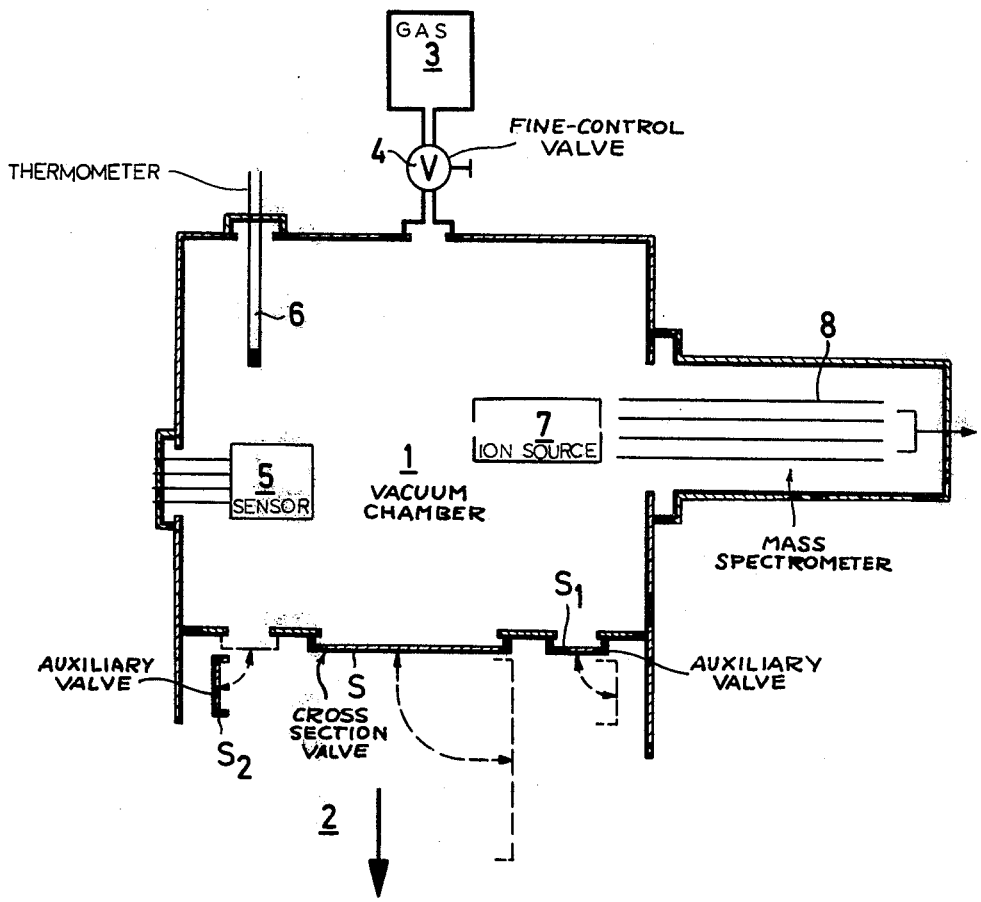

The experiments using the apparatus of FIG. 2, the ion source 7 can be looked at as an emitter of the molecules CD when a cluster flow through the chamber 1 is generated. The measurement curve is a composite e-function.

Upon attainment of a steady state, there are, in the chamber 1, not only clusters $(CD)_x$ but also molecules CD of the gas. Upon the opening of the second auxiliary valve, the lighter gas molecules CD flow more rapidly from the chamber 1 than the heavier clusters $(CD)_x$. The density decreases at t=0, predominantly a result of the density change caused by the preferential departure of the component CD.

The flow curve for the light component can be calculated and extracted from the experimentally derived total curve based upon the density change and the new experiment conditions. The difference curve is thus the flow curve for the heavier components which is sought.

Figure 3:
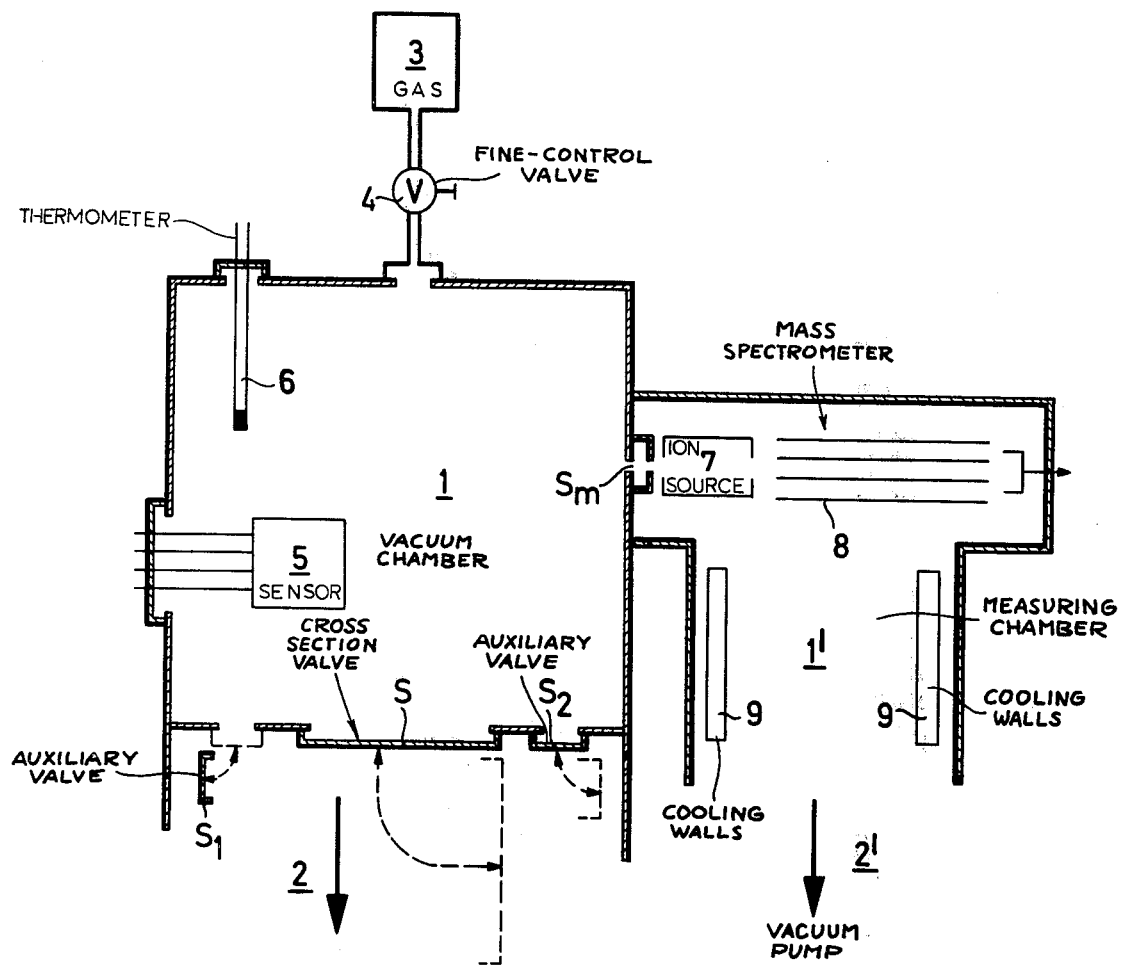

The above-described correction complicates somewhat the evaluation of the results obtained in the analysis of clusters and creates an additional source of error. In FIG. 3, however, there is shown a system which avoids this additional error source and wherein cluster fragments have no effect on the measurement or at most a reduced influence thereon.

In the embodiment of FIG. 3 the mass spctrometer is of the quadrupol type and is shown at 8 by be provided with the ion source 7 and disposed in a separate measuring chamber 1'. The measuring chamber 1' is evacuated by a second pump system 2'.

To hold the backflow from the measuring chamber 1' into the flow chamber 1 as small as possible, the pressure in the measuring chamber 1' must be 1 to 2 powers of 10 smaller than the pressure in the flow chamber 1. In other words, if the pressure in flow chamber 1 is $10^{-7}$, the pressure in chamber 1' should be $10^{-8}$ to $10^{-9}$.

A small opening or window $S_m$ is provided between the chambers 1 and 1' and the gas is permitted to flow as a molecular stream from the flow chamber 1 into the measuring chamber 1'. The ion source 7 of the mass spectrometer is provided directly in this stream and is traversed axially thereby. The cluster fragments generated in the ion source 7 are more rapidly pumped from the measuring chamber 1' by the pump 2' than in the simpler device of FIG. 2. The increase in the partial pressure of the fragment molecules in chamber 1' is sharply limited by providing cooling means therein such as cooling coils, plates or chamber walls 9 which are supplied with a refrigerant or cooling agent, preferably the cryogenic temperatures from a cryostat, liquefied air or liquefied helium source. This makes any return flow to the ion source negligible. The system of FIG. 3 thus has the advantage that the mass spectrometer directly indicates the cluster density in the flow chamber 1 so that an additional calculation for correction is not required.

Figure 4:
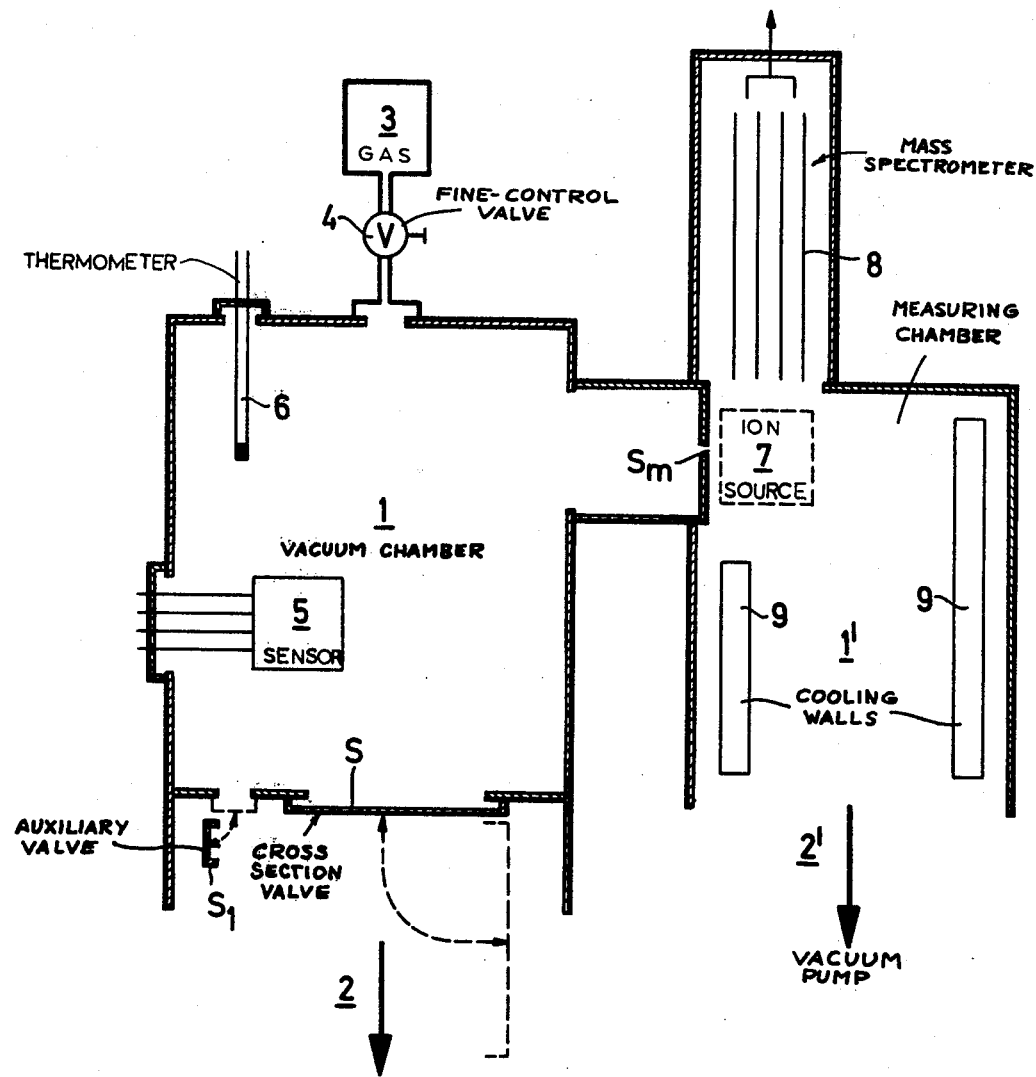

FIG. 4 shows a device which is generally similar to that of FIG. 3 although in this case the ion source is perpendicular to the molecular stream passing through the flow window $S_m$. In this embodiment the unnecessary auxiliary valve $S_2$ is omitted.

Hydrocarbon molecules, like clusters, decompose in the ion source, thereby interfering with the use of mass spectrometry to analyze for hydrocarbon molecules. With the system of the present invention this disadvantage is eliminated since one can distinguish between the hydrocarbon molecules and the decomposed fragments precisely in the same way one is able to distinguish between clusters and the simple molecule CD.

In the following specific Examples, the chamber 1 was a cylindrical vacuum chamber of $V_2A$ steel with a volume of 40000 cm$^3$, a diameter of about 40000 cm and a height of about 35 cm.

The opening cross sections of the auxiliary valves were about 2 cm$^2$.

EXAMPLE I

A SIMS-Auger vacuum chamber of the above description and augmented by two auxiliary valves also used in the diagrammatic configuration shown in FIG. 2. At a constant flow rate, for the gases $O_2$, $N_2$, NO, A and $CO_2$, the gradient $(dJ/dt)_{t=0}$ after opening of the second auxiliary and the difference $\Delta J$ at a pressure of about 7 times $10^{-8}$ Torr, and a temperature of 298K were obtained. The results are given in Table I below.

The values from column 2 show for lines 14 and 28 that the same molecule is involved. The same applies for lines 16 and 32 and 20 and 40. Column 6 shows a factor of 2 for lines 14, 16 and 20. That is the advantage developed from the molecules of lines 28, 32 and 40. The lines 14 and 16 are thus produced by the splitting of the nitrogen and oxygen molecules, line 20 represents the argon molecule in a double-charged state. The doubling of the charge of the ion thus has the same effect as halving the molecule.

Table 1

| m/e | $(dJ/dt)_{t=0}/\Delta J$ | $\frac{(\bar{w})}{\bar{w}_{32m}}$ | $\frac{(\bar{w})}{\bar{w}_{32g}}$ | $\sqrt{H}$ | H |
|-----|-----|-----|-----|-----|---|
| 14  | 0.761 | 1.06 | 1.52 | 1.43 | 2 |
| 16  | 0.715 | 0.99 | 1.42 | 1.43 | 2 |
| 20  | 0.630 | 0.87 | 1.26 | 1.44 | 2 |
| 28  | 0.763 | 1.06 | 1.07 | 1.01 | 1 |
| 30  | 0.752 | 1.03 | 1.03 | 1.00 | 1 |
| 32  | 0.720 | 1.00 | 1.00 | 1.00 | 1 |
| 40  | 0.639 | 0.89 | 0.89 | 1.00 | 1 |
| 44  | 0.593 | 0.82 | 0.84 | 1.03 | 1 |

Comments with respect to Table 1:

Column 1 = the lines of the mass spectrum m/e (mass-/charge ratio.

Column 2 = experimentally determined ratio of $(dJ/dt)_{t=0}/\Delta J$. This measurement is an average of several measurements with the mean deviation about 1%.

Column 3 = the ratio of the mean molecule velocity w to the molecular velocity of oxygen $\bar{w}_{32}$.

Column 4 = the ratio $(w/w_{32})_0$ calculated from the gas kinetic data.

Column 5 = the ratio $V\bar{y}1$ determined from the numerical values of columns 3 and 4 and particularly the ratio of the value in column 4 to that of column 3.

Column 6 = the separation factor of the molecule in the ion source.

EXAMPLE 2

The gas analyzed was carbon tetrachloride.

The carbon tetrachloride supplied to a mass spectrometer gives a line-rich spectrum with intensive lines at atomic mass units of 35, 37, 47, 47; 82, 84, 86 and 117, 119, 121, 123 which derive from fragment ions of the carbon tetrachloride molecule. These fragments are primarily produced by electron bombardment in the ion source.

The carbon tetrachloride spectrum is evaluated as described above. The flow rate of the carbon tetrachloride is held constant and, at a constant temperature, change with time of the line intensities after opening of the second valve is determined. A semilogarithmic plot with time shows one and the same slope for the lines 34, 37; 47, 47; 82, 84, 86 and 117, 119, 121, 123. As a result it can be concluded that these lines belong to one and the same parent molecule.

To detect the molecular weight of the parent molecule, a reference gas, namely oxygen is introduced under the same flow conditions and, at the same temperature.

If these results are plotted on the same semilogarithmic graph, the result is a curve which intersects the beginning of the carbon tetrachloride curve but is somewhat steeper. Calculation shows that the mass of the parent molecule lies between $$(5.3/2.45)^2 \cdot 32 = 150$$

$$(5.4/2.4)^2 \cdot 32 = 162$$

atomic mass units. The spectrum is found to contain weak lines at 152, 154, 156, 158 and 160 which are associated with the parent molecule.

I claim:

1. A method of analyzing a gas comprising the steps of:

(a) feeding the gas to be analyzed into a first zone of known volume and permitting the gas in said zone to escape in a Knudsen flow through a first cross section into a second zone at a predetermined pressure;

(b) permitting the gas flow into and from the first zone in step (a) to reach a first steady state;

(c) measuring a parameter of the gas in said first zone at said first steady state;

(d) spontaneously changing the flow cross section through which said gas escapes from said first zone upon attainment of said first steady state and permitting the gas flow into said first zone and through the changed cross section to reach a second steady state;

(e) measuring said parameter of the gas at said second steady state; and (f) deriving from said measurements values of the difference between the measurements at said steady states and the gradient of the measured value upon the spontaneous change in the cross section, the molecular weight of the gas and the mean molecular velocity thereof being functions of said difference and gradient.

2. The method defined in claim 1 wherein the spontaneous change in the flow cross section in step (d) is an increase in the flow cross section.

3. The method defined in claim 2 wherein the volume of the first zone, the pressure in said second zone and the feed rate of the gas to the first zone are held constant.

4. The method defined in claim 2 wherein the volume of the first zone, the pressure in said second zone or the feed rate of the gas to the first zone are held constant.

5. The method defined in claim 2 wherein steps (a) through (e) are repeated for a succession of cross sectional changes with the gradient and the difference between each new and previous steady state being determined in step (f) for each repetition.

6. The method defined in claim 5 wherein each change in cross section is by the same amount.

7. The method defined in claim 2 wherein said parameter is the gas density.

8. The method defined in claim 2 wherein said parameter is a parameter proportional to gas density.

9. The method defined in claim 2 wherein said first zone is evacuated to a pressure of $10^{-5}$ to $10^{-9}$ torr.

10. The method defined in claim 9 wherein said pressure is of the order of $10^{-7}$ torr.

11. The method defined in claim 1 wherein steps (c), (e) and (f) are carried out automatically.

12. The method defined in claim 1 wherein step (f) is carried out at least in part by plotting the change in the measurement of said parameter as a function of time upon spontaneous change in the flow cross section in step (d).

13. The method defined in claim 1 wherein said parameters are measured and an electric signal representing same is generated, said difference being the difference in the magnitude of the electrical signals from the measurements at said first and second steady states.

14. An apparatus for analyzing a gas, comprising:
a vacuum chamber having a defined volume;
means for feeding said chamber with a gas to be analyzed at a constant flow rate;
means for evacuating said chamber;
valve means defining a first flow cross section and a second flow cross section and connecting same selectively between said evacuating means and said chamber whereby a first Knudsen flow is established through at least one of said cross sections and the other cross section is selectively openable and closable to change the Knudsen cross-section at which gas escapes from said chamber; and
a sensor for gas density in said chamber.

15. The apparatus defined in claim 14 wherein said valve means includes a pair of valves each defining one of said cross sections and having the same effective cross section in the open state.

16. The apparatus defined in claim 14 wherein said feeding means includes a source of said gas and a control valve between said source and said chamber for maintaining the feed rate constant.

17. The apparatus defined in claim 16 wherein said valve means further comprises a valve formed with a large cross section and openable for evacuation of said chamber prior to the feed of said gas thereto.

18. The apparatus defined in claim 17 which is constituted as an ultra-high vacuum apparatus.

19. The apparatus defined in claim 17 wherein said sensor is the ion source of a mass spectrometer connected to said chamber.

20. The apparatus defined in claim 19 wherein said sensor is disposed in a measuring chamber connected to said vacuum chamber by a window with a small effective flow cross section, said ion source being disposed downstream of said window.

21. The apparatus defined in claim 20 wherein said mass spectrometer is disposed axially of the molecular flow through said window.

22. The apparatus defined in claim 20 wherein said mass spectrometer extends normal to the molecular flow through said window.

23. The apparatus defined in claim 20, further comprising means for evacuating said measuring chamber to a pressure at least one to two powers of ten below that of said vacuum chamber.

* * * * *